(12) United States Patent
Li et al.

(10) Patent No.: US 12,076,146 B2
(45) Date of Patent: Sep. 3, 2024

(54) BIOLOGICAL FLUID SEPARATION DEVICE

(71) Applicant: Becton, Dickinson and Company, Franklin Lakes, NJ (US)

(72) Inventors: Peng Li, Ridgewood, NJ (US); Scott Wentzell, Suffern, NY (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 797 days.

(21) Appl. No.: 17/059,598

(22) PCT Filed: Jun. 6, 2019

(86) PCT No.: PCT/US2019/035761
§ 371 (c)(1),
(2) Date: Nov. 30, 2020

(87) PCT Pub. No.: WO2019/236822
PCT Pub. Date: Dec. 12, 2019

(65) Prior Publication Data
US 2021/0161448 A1   Jun. 3, 2021

Related U.S. Application Data

(60) Provisional application No. 62/681,894, filed on Jun. 7, 2018.

(51) Int. Cl.
*A61B 5/15*   (2006.01)

(52) U.S. Cl.
CPC .... *A61B 5/150755* (2013.01); *A61B 5/15003* (2013.01); *A61B 5/150213* (2013.01); *A61B 5/150251* (2013.01); *A61B 5/150351* (2013.01)

(58) Field of Classification Search
CPC .......... A61B 5/150755; A61B 5/15003; A61B 5/150213; A61B 5/150251; A61B 5/150351; B01L 3/502
See application file for complete search history.

(56) References Cited

U.S. PATENT DOCUMENTS 8,741,234 B2   6/2014   Wang et al.
9,028,688 B2   5/2015   Okamoto et al.
(Continued)

FOREIGN PATENT DOCUMENTS

CN   101189515 A   5/2008
CN   102985175 A   3/2013
(Continued)

OTHER PUBLICATIONS

Huang et al., "Separation of blood plasma by inertial focusing using microfluidic chips", Chinese Science Bulletin, 2011, pp. 1711-1719, vol. 56. (English-language abstract).
(Continued)

*Primary Examiner* — Devin B Henson
(74) *Attorney, Agent, or Firm* — The Webb Law Firm

(57) ABSTRACT

A blood separation device that decouples and separates the blood collection process from the plasma separation process is disclosed. The blood separation device includes a sample collection module, an activation module, and a separation module. Because the plasma separation happens after the blood separation device is disconnected from a patient, the device performance is no longer affected by patient blood pressure and needle gauge, and patient discomfort is greatly reduced.

23 Claims, 12 Drawing Sheets

(56) References Cited

U.S. PATENT DOCUMENTS

| | | |
|---|---|---|
| 9,283,313 B2 | 3/2016 | Huemer |
| 9,427,707 B2 | 8/2016 | Montagu et al. |
| 9,486,416 B2 | 11/2016 | Winchester et al. |
| 9,597,028 B2 | 3/2017 | Marchiarullo et al. |
| 10,687,750 B2 | 6/2020 | Schuetz et al. |
| 11,000,846 B2 | 5/2021 | Roxhed et al. |
| 11,076,787 B2 * | 8/2021 | Bullington ....... A61B 5/150251 |
| 2002/0049391 A1 | 4/2002 | Kuracina et al. |
| 2008/0017577 A1 | 1/2008 | Yi et al. |
| 2013/0026085 A1 * | 1/2013 | Samsoondar .......... B01D 63/02 |
| | | 210/136 |
| 2014/0305196 A1 | 10/2014 | Ellis et al. |
| 2015/0342510 A1 * | 12/2015 | Bullington ....... A61B 5/150251 |
| | | 600/575 |
| 2017/0035337 A1 | 2/2017 | Wilkinson et al. |
| 2017/0087517 A1 | 3/2017 | McNeely |
| 2017/0203014 A1 | 7/2017 | Kenley |
| 2017/0354362 A1 * | 12/2017 | Xu ....................... G01N 33/491 |
| 2018/0049686 A1 | 2/2018 | Marchiarullo et al. |

FOREIGN PATENT DOCUMENTS

| | | |
|---|---|---|
| CN | 103185689 A | 7/2013 |
| CN | 104107060 A | 10/2014 |
| CN | 104146715 A | 11/2014 |
| CN | 104519976 A | 4/2015 |
| CN | 105263540 A | 1/2016 |
| CN | 106108920 A | 11/2016 |
| CN | 107923905 A | 4/2018 |
| JP | 20059888 A | 1/2005 |
| JP | 2008279195 A | 11/2008 |
| JP | 2015528328 A | 9/2015 |
| WO | 2016145057 A1 | 9/2016 |
| WO | 2016205779 A2 | 12/2016 |

OTHER PUBLICATIONS

Liu et al., "Simple negative-pressure vacuum flask plasma separation method", Journal of Weifang Medical College, 1989, pp. 78-79, vol. 11, No. 2.

* cited by examiner

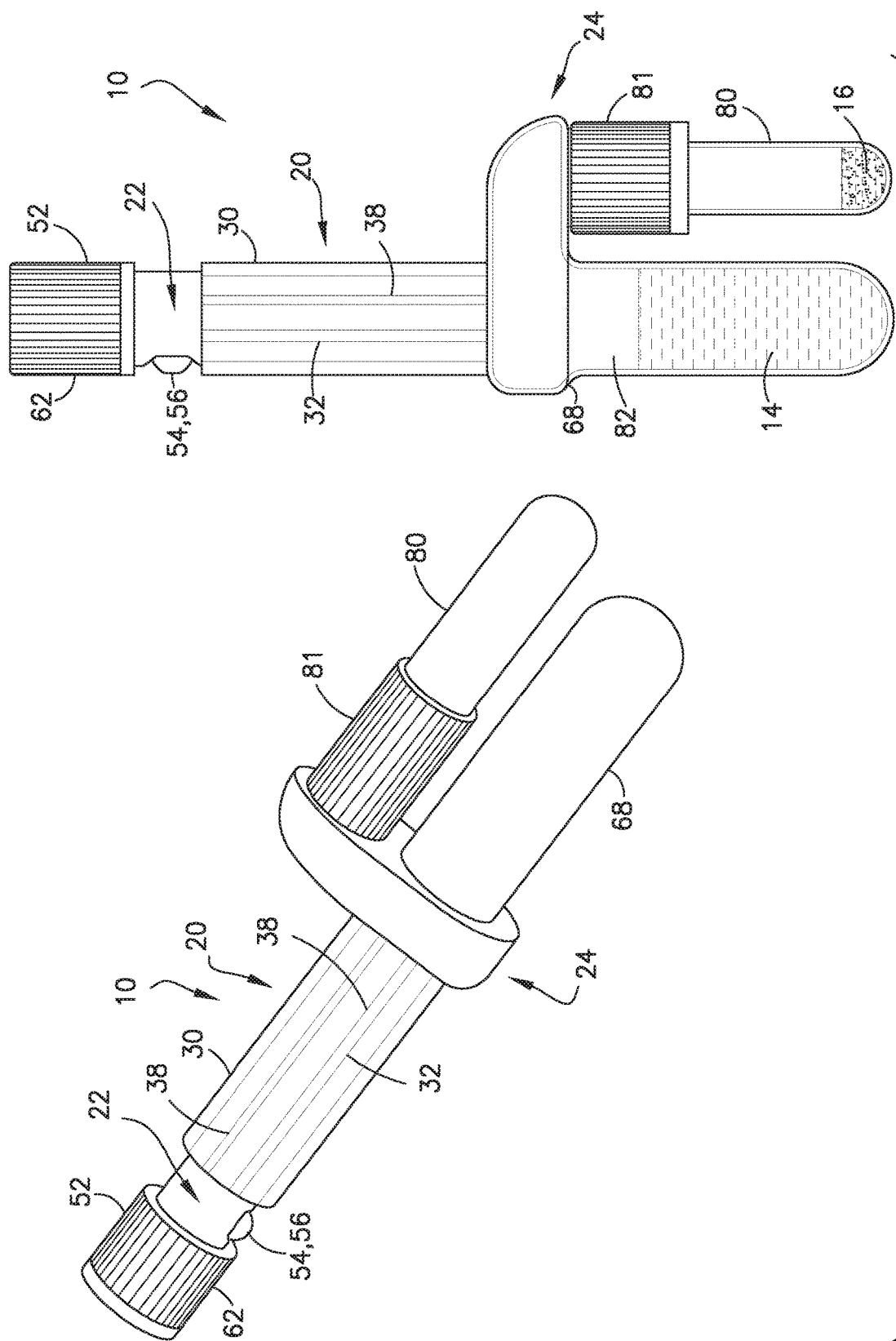

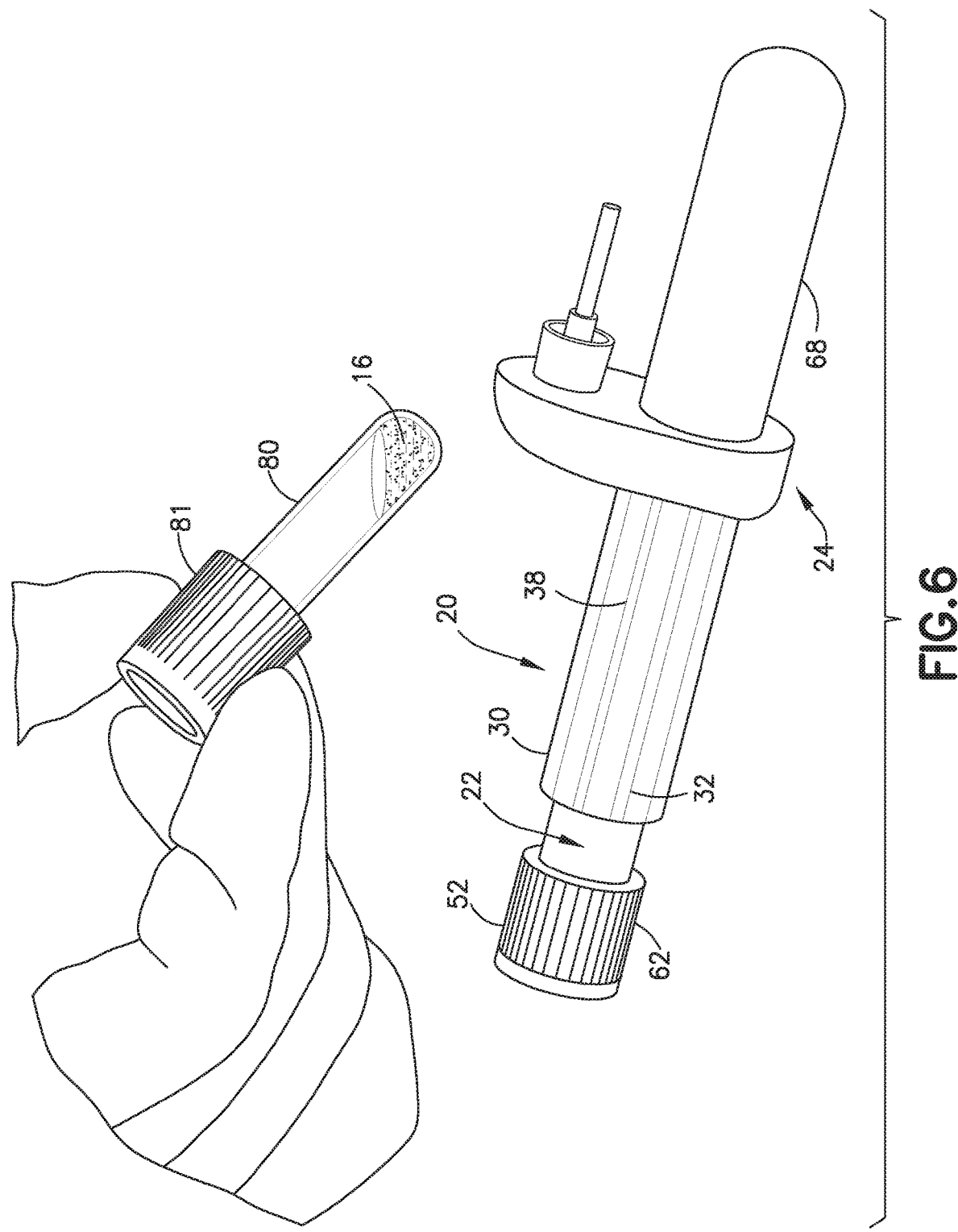

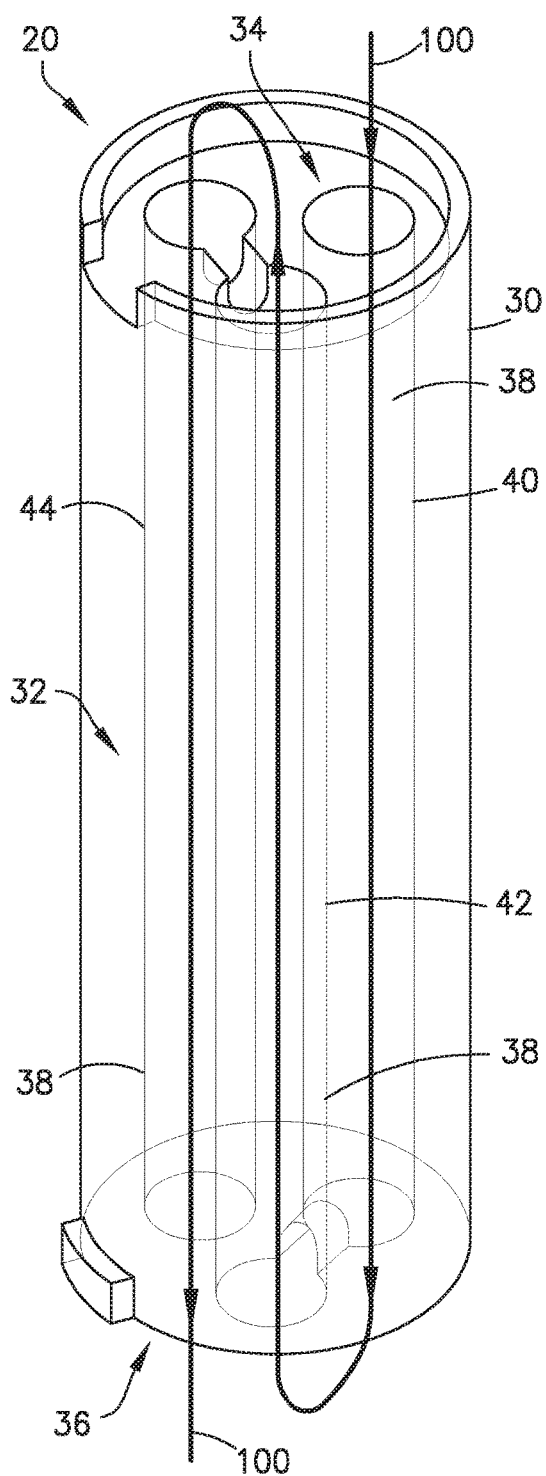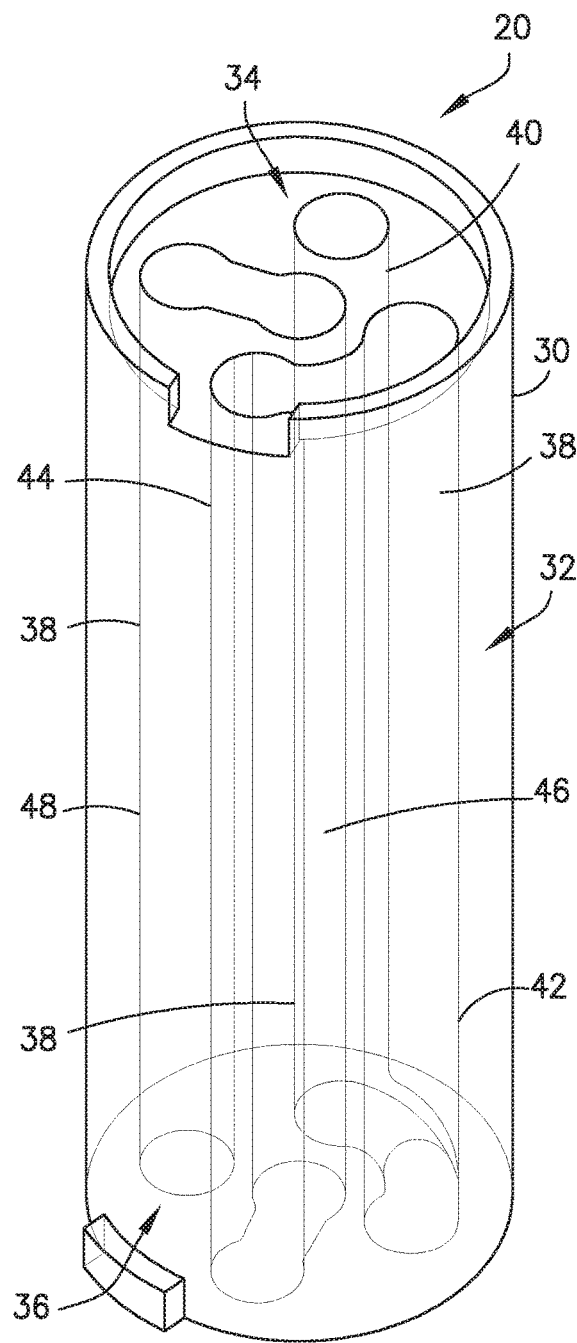
FIG.9
FIG.10

BIOLOGICAL FLUID SEPARATION DEVICE

CROSS-REFERENCE TO RELATED APPLICATIONS

This application is the United States national phase of International Application No. PCT/US2019/035761 filed Jun. 6, 2019, and claims priority to U.S. Provisional Application Ser. No. 62/681,894, entitled "Biological Fluid Separation Device", filed Jun. 7, 2018, the entire disclosures of which are hereby incorporated by reference in their entirety.

BACKGROUND OF THE INVENTION

1. Field of the Disclosure

The present disclosure relates generally to devices adapted for use with biological fluids. More particularly, the present disclosure relates to devices adapted for separating components of biological fluids.

2. Description of the Related Art

Blood sampling is a common health care procedure involving the withdrawal of at least a drop of blood from a patient. Blood samples are commonly taken from hospitalized, homecare, and emergency room patients either by finger stick, heel stick, or venipuncture. Blood samples may also be taken from patients by venous or arterial lines. Once collected, blood samples may be analyzed to obtain medically useful information including chemical composition, hematology, or coagulation, for example.

Blood tests determine the physiological and biochemical states of the patient, such as disease, mineral content, drug effectiveness, and organ function. Blood tests may be performed in a clinical laboratory or at the point-of-care near the patient. One example of point-of-care blood testing is the routine testing of a patient's blood glucose levels which involves the extraction of blood via a finger stick and the mechanical collection of blood into a diagnostic cartridge. Thereafter, the diagnostic cartridge analyzes the blood sample and provides the clinician a reading of the patient's blood glucose level. Other devices are available which analyze blood gas electrolyte levels, lithium levels, and ionized calcium levels. Some other point-of-care devices identify markers for acute coronary syndrome (ACS) and deep vein thrombosis/pulmonary embolism (DVT/PE).

Blood samples contain a whole blood or cellular portion and a plasma portion. Plasma separation from whole blood has been traditionally achieved by centrifugation which typically takes 15 to 20 minutes and involves heavy labor or complex work flow. Recently there are other technologies that have been used or tried to separate plasma such as sedimentation, fibrous or non-fibrous membrane filtration, lateral flow separation, microfluidics cross flow filtration and other microfluidics hydrodynamic separation techniques. However many of those technologies have various challenges arranging from poor plasma purity, analyte bias or requiring specific coating to prevent analyte bias, high hemolysis, requiring dilution, long separation time, and/or difficult to recover the plasma. For example, most membrane based separation technologies suffer from an analyte bias problem, and often require specific coating treatments for the target analytes. Additionally, conventional separation technologies that occur while the device is directly connected to a patient thru a needle cause patient discomfort.

SUMMARY OF THE INVENTION

The present disclosure provides a blood separation device that decouples and separates the blood collection process from the plasma separation process. The blood separation device includes a sample collection module, an activation module, and a separation module. Because the plasma separation happens after the blood separation device is disconnected from a patient, the device performance is no longer affected by patient blood pressure and needle gauge, and patient discomfort is greatly reduced.

The present disclosure provides a blood separation device and a separation process that is fully compatible with a venous blood collection workflow without the need of centrifugation and power. Advantageously, the blood separation device of the present disclosure allows for the immediate separation of plasma during clinical blood draws and the ability for collection of the separated plasma sample in a self-contained plasma container for downstream diagnostics.

Furthermore, the blood separation device of the present disclosure provides for a separation device that only needs a short on-patient collection time that is no different than a conventional blood collection device using vacuum tubes, such as a BD Vacutainer® blood collection tube commercially available from Becton, Dickinson and Company, and corresponding venous access sets. Additionally, since the plasma separation happens after the device is disconnected from the patient, the device performance is no longer affected by patient blood pressure and needle gauge, and patient discomfort is greatly reduced.

Because the blood separation device of the present disclosure decouples and separates the blood collection process from the plasma separation process, the volume of the plasma generated is no longer limited by the allowable blood collection time on-patient. This enables the potential use of the blood separation device of the present disclosure for other high volume plasma applications beyond point of care.

Furthermore, another benefit of decoupling the separation from the collection process is that the separation time, plasma quality, and yield is no longer affected by the needle gauge and patient blood pressure. If the separation happens while a device is directly connected to a patient thru a needle, lower needle gauge and higher patient blood pressure reduce the separation time, yield and increases the hemolysis, whereas higher needle gauge and lower patient blood pressure increases the separation time, yield and decreases the hemolysis. By isolating the plasma separation process from the blood collection workflow using a blood separation device of the present disclosure, the blood collection sets and patient blood pressure will only affect the blood collection time while not varying the separation time, yield and hemolysis level.

In accordance with an embodiment of the present invention, a blood separation device adapted to receive a blood sample having a first phase and a second phase includes a sample collection module having a housing defining a collection chamber; an activation module connected to the sample collection module, the activation module having a first seal and a second seal for sealing the housing, the first seal transitionable from a closed position in which the collection chamber has a first pressure to an open position, by actuation of a portion of the activation module, in which the collection chamber is in fluid communication with a second pressure greater than the first pressure; and a separation module in fluid communication with the collection chamber of the sample collection module, the separation module defining a first chamber having a first volume and a second chamber having a second volume and including a separation member disposed between the first chamber and the second chamber, wherein the first volume and the second volume are different.

In one configuration, the activation module includes a switch, wherein actuation of the switch transitions the first seal to the open position. In another configuration, the switch comprises a push button defining a vent hole therethrough and a piercing portion, wherein actuation of the switch moves the piercing portion to break the first seal thereby transitioning the first seal to the open position. In yet another configuration, with the first seal in the open position, the collection chamber of the sample collection module is in fluid communication with the second pressure via the vent hole of the switch. In one configuration, the second seal comprises a cap having a pierceable self-sealing stopper within a portion of the cap. In another configuration, the blood separation device is connectable to a blood collection device via the cap. In yet another configuration, the activation module defines an inlet channel, and wherein with the blood collection device connected to the blood separation device via the cap, the collection chamber receives the blood sample via the inlet channel. In one configuration, the collection chamber includes an inlet end and an exit end and defines a plurality of sequential flow direction alternating collection channels. In another configuration, the collection chamber includes an inlet end and an exit end and defines a first collection channel extending from the inlet end to the exit end, a second collection channel in communication with a portion of the first collection channel and extending from the exit end to the inlet end, and a third collection channel in communication with a portion of the second collection channel and extending from the inlet end to the exit end. In yet another configuration, the inlet end of the collection channels is in fluid communication with the inlet channel of the activation module. In one configuration, the blood sample travels through the first collection channel in a first direction, the blood sample travels through the second collection channel in a second direction opposite the first direction, and the blood sample travels through the third collection channel in a third direction opposite the second direction. In another configuration, the first collection channel is spaced from the second collection channel which is spaced from the third collection channel. In yet another configuration, the first chamber includes a first chamber inlet and a first chamber outlet, and the second chamber includes a second chamber outlet. In one configuration, the first chamber inlet is in fluid communication with the exit end of the collection channels. In another configuration, with the first seal in the open position, a first pressure difference between the second pressure defined by atmospheric pressure and the first pressure defined within the collection chamber draws the blood sample into the first chamber. In yet another configuration, with the first seal in the open position, the first volume and the second volume being different provides a second pressure difference between the first chamber and the second chamber to drive the second phase of the blood sample through the separation member into the second chamber. In one configuration, the separation member traps the first phase in the first chamber and allows the second phase to pass through the separation member into the second chamber. In another configuration, the blood separation device includes a second phase collection container in communication with the second chamber outlet, wherein the second phase collection container receives the second phase. In yet another configuration, the blood separation device includes a blood sample discard chamber in communication with the first chamber outlet, wherein the blood sample discard chamber receives the first phase. In one configuration, the separation member comprises a track-etched membrane. In another configuration, with the blood collection device connected to the blood separation device via the cap, the collection chamber receives the blood sample via the inlet channel. In yet another configuration, with the blood collection device disconnected from the blood separation device, and wherein upon actuation of the switch to transition the first seal to the open position, the first pressure difference between the second pressure defined by atmospheric pressure and the first pressure defined within the collection chamber draws the blood sample into the first chamber. In one configuration, with the first seal in the open position, the first volume and the second volume being different provides the second pressure difference between the first chamber and the second chamber to drive the second phase of the blood sample through the separation member into the second chamber. In another configuration, with the second phase contained within the second phase collection container, the second phase collection container is removable from the blood separation device. In yet another configuration, the first phase is a cellular portion and the second phase is a plasma portion.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 5 is a perspective view of a third step of using a system of the present disclosure illustrating the device of the present disclosure separates plasma independent of the device orientation in accordance with an embodiment of the present invention.

FIG. 6 is a perspective view of a fourth step of using a system of the present disclosure in accordance with an embodiment of the present invention.

FIG. 9 is a perspective view of a collection chamber of a blood separation device in accordance with an embodiment of the present invention.

FIG. 10 is a perspective view of a collection chamber of a blood separation device in accordance with another embodiment of the present invention.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
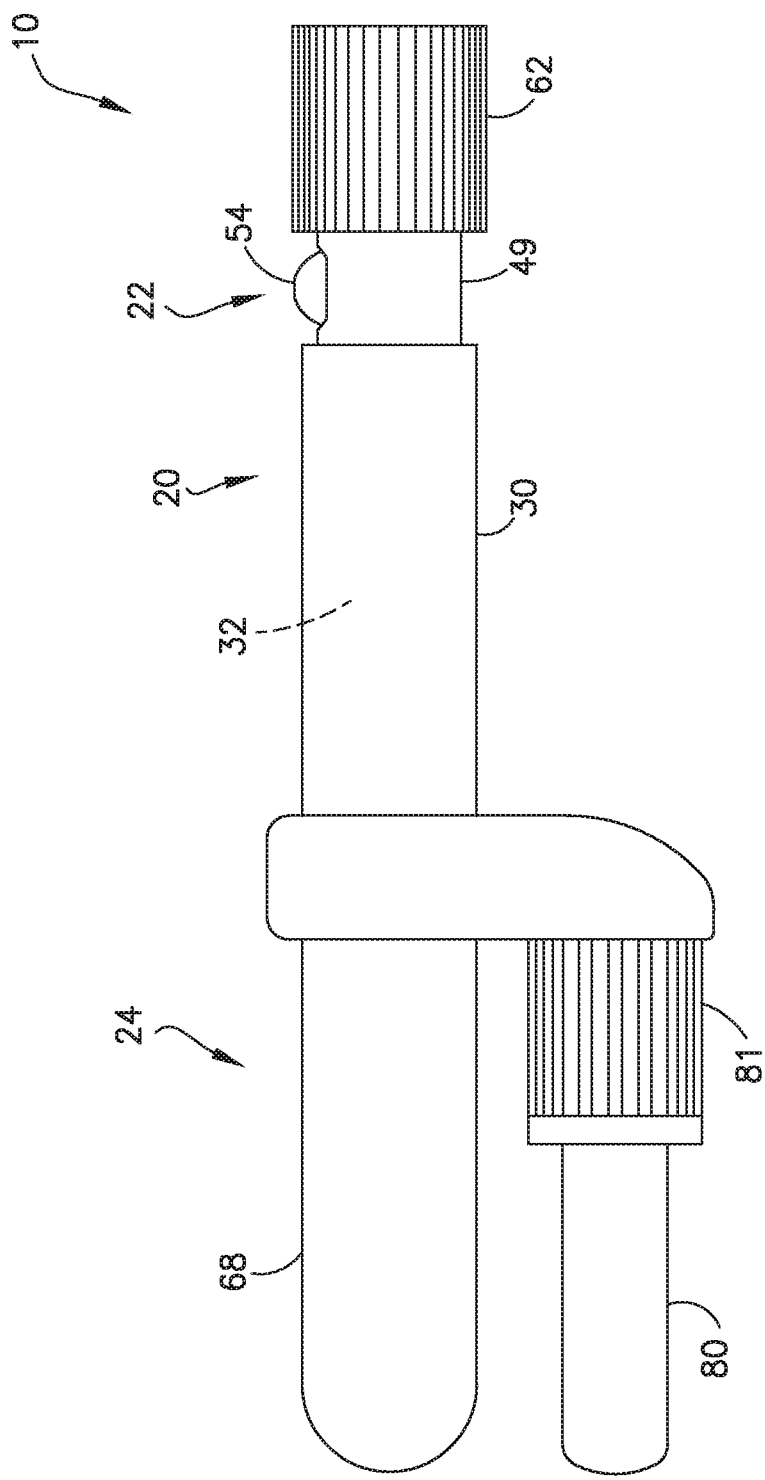
FIG. 1 is a perspective view of a blood separation device in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

Figure 2:
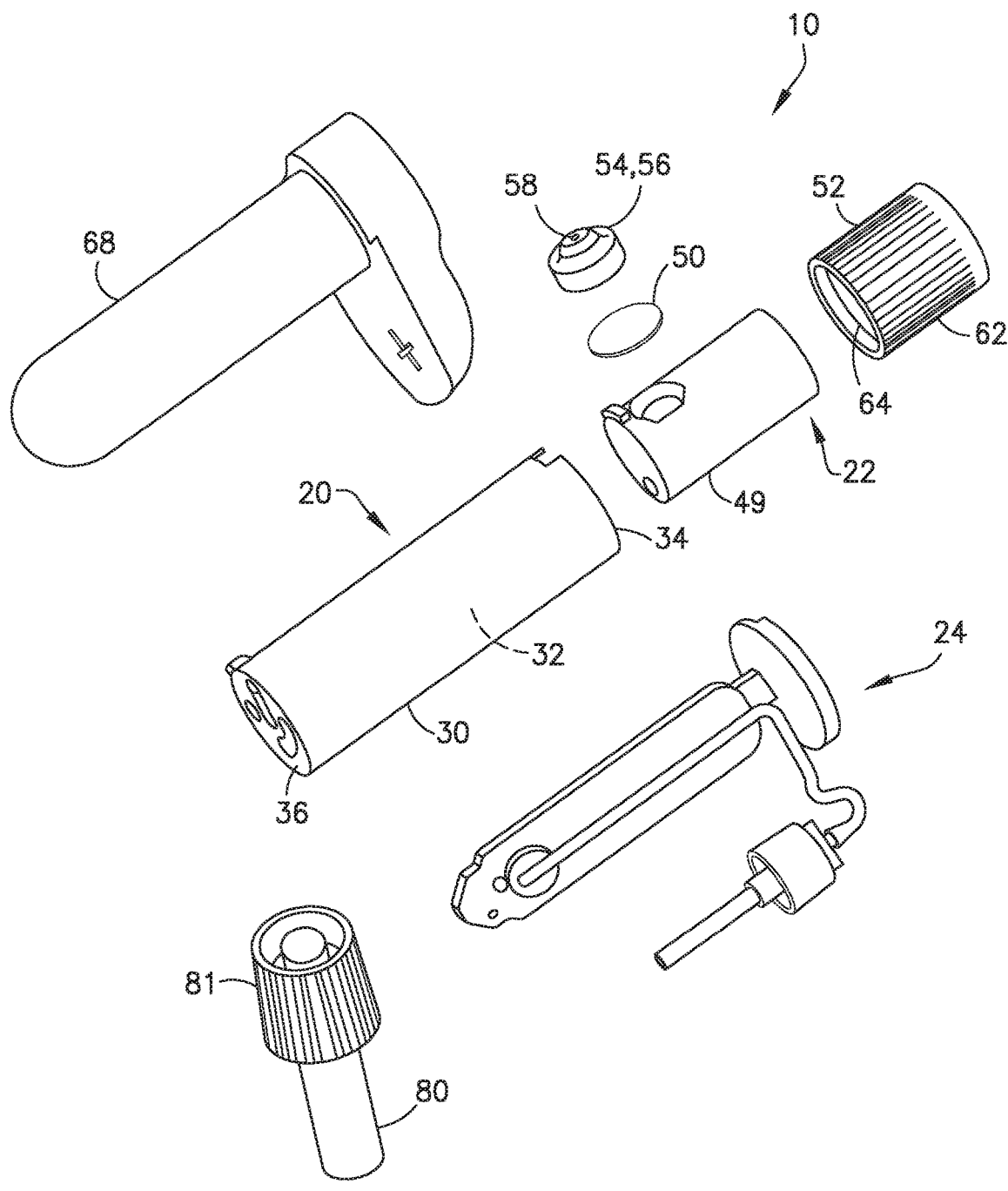
FIG. 2 is an exploded, perspective view of a blood separation device in accordance with an embodiment of the present invention.

FIGS. 1 and 2 illustrate an exemplary embodiment of a blood separation device of the present disclosure. Referring to FIGS. 1 and 2, a blood separation device 10 of the present disclosure is adapted to receive a biological fluid, such as a blood sample 12 (FIGS. 3-6) having a first phase 14 and a second phase 16. The first phase 14 of the blood sample 12 is a cellular portion and the second phase 16 of the blood sample 12 is a plasma portion.

A blood separation device 10 of the present disclosure decouples and separates the blood collection process from the plasma separation process. Because the plasma separation happens after the blood separation device 10 is disconnected from a patient, the device performance is no longer affected by patient blood pressure and needle gauge, and patient discomfort is greatly reduced.

Because the blood separation device 10 of the present disclosure decouples and separates the blood collection process from the plasma separation process, the volume of the plasma generated is no longer limited by the allowable blood collection time on-patient. This enables the potential use of the blood separation device 10 of the present disclosure for other high volume plasma applications beyond point of care.

The present disclosure provides a blood separation device 10 and a separation process that is fully compatible with a venous blood collection workflow without the need of centrifugation and power. Advantageously, the blood separation device 10 of the present disclosure allows for the immediate separation of plasma during clinical blood draws, with the device 10 off-patient, and the ability for collection of the separated plasma 16 sample in a self-contained plasma container, e.g., a second phase or plasma collection container 80, for downstream diagnostics.

Furthermore, the blood separation device 10 of the present disclosure provides for a separation device that only needs a short on-patient collection time that is no different than a conventional blood collection device using vacuum tubes, such as a BD Vacutainer® blood collection tube commercially available from Becton, Dickinson and Company, and corresponding venous access sets. Additionally, since the plasma separation happens after the device 10 is disconnected from the patient, the device performance is no longer affected by patient blood pressure and needle gauge, and patient discomfort is greatly reduced.

Furthermore, another benefit of decoupling the plasma separation process from the collection process is that the separation time, plasma quality, and yield is no longer affected by the needle gauge and patient blood pressure. If the plasma separation process occurs while a device is directly connected to a patient thru a needle, lower needle gauge and higher patient blood pressure reduce the separation time, yield and increases the hemolysis, whereas higher needle gauge and lower patient blood pressure increases the separation time, yield and decreases the hemolysis. By isolating the plasma separation process from the blood collection process using a blood separation device 10 of the present disclosure, the blood collection sets and patient blood pressure will only affect the blood collection time while not varying the separation time, yield and hemolysis level.

Referring to FIGS. 1-13, in an exemplary embodiment, a blood separation device 10 generally includes a sample collection module 20, an activation module 22, and a separation module 24. In one embodiment, after collecting a blood sample 12, the blood separation device 10 is able to separate a second phase 16 of the blood sample 12 from a first phase 14 of the blood sample 12 as described in more detail below. Advantageously, the blood separation device 10 decouples and separates the blood collection process from the plasma separation process. In one embodiment, after plasma separation, a portion that is removable, e.g., a second phase collection container 80, from the blood separation device 10 is able to transfer the second phase 16 of the blood sample 12 to a point-of-care testing device.

Referring to FIGS. 1-6 and 9-11, in an exemplary embodiment, the sample collection module 20 includes a housing 30 defining a collection chamber 32. In one embodiment, the collection chamber 32 includes an inlet end or inlet 34 and an exit end or exit 36 and defines a plurality of sequential flow direction alternating collection channels 38.

Figure 11:
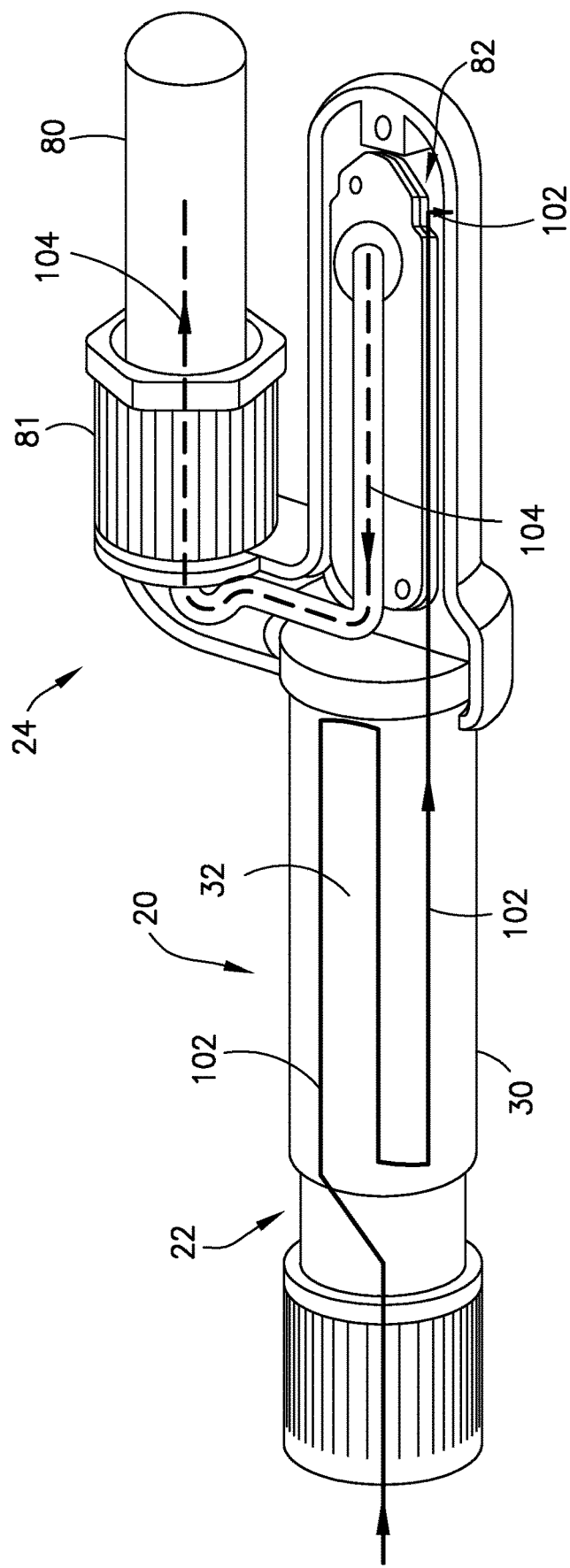
FIG. 11 is a perspective view of a blood separation device in accordance with an embodiment of the present invention.

The collection chamber 32 utilizes multiple interconnected parallel channels 38 to maximize collection and storage space within the constrained diameter of a blood collection set and also to ensure that the capillary force dominates over gravity during filling. A blood sample 12 fills the interconnected channels 38 of the sample collection module 20 in a back-and-forth motion as shown in FIGS. 9-11.

For example, referring to FIG. 9, in a first exemplary embodiment, the collection chamber 32 of the sample collection module 20 defines a first collection channel 40 extending from the inlet end 34 to the exit end 36, a second collection channel 42 in communication with a portion of the first collection channel 40 and extending from the exit end 36 to the inlet end 34, and a third collection channel 44 in communication with a portion of the second collection channel 42 and extending from the inlet end 34 to the exit end 36. Referring to FIG. 9, the first collection channel 40 is spaced from the second collection channel 42 which is spaced from the third collection channel 44.

In this manner, referring to the arrow in FIG. 9 indicating a flow path 100 of the blood sample 12 through the channels 38 of the collection chamber 32, a blood sample 12 collected into the collection chamber 32 travels through the first collection channel 40 in a first direction, the blood sample 12 travels through the second collection channel 42 in a second direction opposite the first direction, and the blood sample 12 travels through the third collection channel 44 in a third direction opposite the second direction. Referring to FIG. 9, the collection chamber 32 utilizes multiple interconnected parallel channels 38 to maximize collection and storage space within the constrained diameter of a blood collection set and also to ensure that the capillary force dominates over gravity during filling.

In one embodiment, the entrance into the collection chamber 32 is the inlet 34 of the first collection channel 40 and the exit out of the collection chamber 32 is the exit 36 of the third collection channel 44. The inlet 34 of the first collection channel 40 is in fluid communication with an inlet channel 66 (FIGS. 7B and 8B) of the activation module 22, as described in more detail below.

Referring to FIG. 10, in a second exemplary embodiment, the collection chamber 32 of the sample collection module 20 defines a first collection channel 40 extending from the inlet end 34 to the exit end 36, a second collection channel 42 in communication with a portion of the first collection channel 40 and extending from the exit end 36 to the inlet end 34, a third collection channel 44 in communication with a portion of the second collection channel 42 and extending from the inlet end 34 to the exit end 36, a fourth collection channel 46 in communication with a portion of the third collection channel 44 and extending from the exit end 36 to the inlet end 34, and a fifth collection channel 48 in communication with a portion of the fourth collection channel 46 and extending from the inlet end 34 to the exit end 36. Referring to FIG. 10, the first collection channel 40 is spaced from the second collection channel 42 which is spaced from the third collection channel 44 which is spaced from the fourth collection channel 46 which is spaced from the fifth collection channel 48.

In this manner, a blood sample 12 collected into the collection chamber 32 travels through the first collection channel 40 in a first direction, the blood sample 12 travels through the second collection channel 42 in a second direction opposite the first direction, the blood sample 12 travels through the third collection channel 44 in a third direction opposite the second direction, the blood sample 12 travels through the fourth collection channel 46 in a fourth direction opposite the third direction, and the blood sample 12 travels through the fifth collection channel 48 in a fifth direction opposite the fourth direction. Referring to FIG. 10, the collection chamber 32 utilizes multiple interconnected parallel channels 38 to maximize collection and storage space within the constrained diameter of a blood collection set and also to ensure that the capillary force dominates over gravity during filling.

In one embodiment, the entrance into the collection chamber 32 is the inlet 34 of the first collection channel 40 and the exit out of the collection chamber 32 is the exit 36 of the fifth collection channel 48. The inlet 34 of the first collection channel 40 is in fluid communication with an inlet channel 66 (FIGS. 7B and 8B) of the activation module 22, as described in more detail below.

In other exemplary embodiments, the collection chamber 32 of the sample collection module 20 may define any odd number of channels 38 based on a specific volume requirement. Importantly, the collection chamber 32 of the sample collection module 20 utilizes multiple interconnected parallel channels 38 to maximize collection and storage space within the constrained diameter of a blood collection set and also to ensure that the capillary force dominates over gravity during filling. A blood sample 12 fills the interconnected channels 38 of the sample collection module 20 in a back-and-forth motion as described above.

In one exemplary embodiment, the plurality of sequential flow direction alternating collection channels 38 are configured in a parallel configuration as shown in FIGS. 9 and 10. In other exemplary embodiments, the collection channels 38 are configured in a spiral or meandering channel configuration or in other configurations that maximize collection and storage space within the constrained diameter of a blood collection set and also to ensure that the capillary force dominates over gravity during filling.

In an exemplary embodiment, the collection chamber 32 is designed to ensure that the blood 12 fills the channels 38 of the collection chamber 32 continuously without trapping air bubbles regardless of device orientation and blood flow rate. This is accomplished by controlling the diameter of the channels 38 for desired applications. For example, in an exemplary embodiment, to prevent the blood stream from breaking up and trapping air bubbles, the diameter of the channels 38 needs to simultaneously meet two requirements. First, the static pressure difference at the flow front at any orientation needs to be smaller than the Laplace pressure so that the meniscus will hold its shape. Second, the selected diameter needs to make sure that the inertia force is smaller than the surface tension at the highest flow rate.

Referring to FIGS. 1, 2, and 7A-8B, in an exemplary embodiment, the activation module 22 is connected or connectable to the sample collection module 20 and includes a housing 49, a first seal 50, and a second seal 52 for sealing the blood separation device 10, e.g., the housing 30 of the sample collection module 20, the housing 49 of the activation module 22, and a housing 68 of the separation module 24. In this manner, the seals 50, 52 of the activation module 22 control the pressure within the blood separation device 10 as described in more detail below. The first seal 50 is transitionable from a closed position (FIGS. 7A and 7B) in which the collection chamber 32 has a first pressure P1 (FIG. 13) to an open position (FIGS. 8A and 8B), by actuation of a portion of the activation module 22, in which the collection chamber 32 is in fluid communication with a second pressure P2 (FIG. 13) greater than the first pressure P1.

Figure 7A:
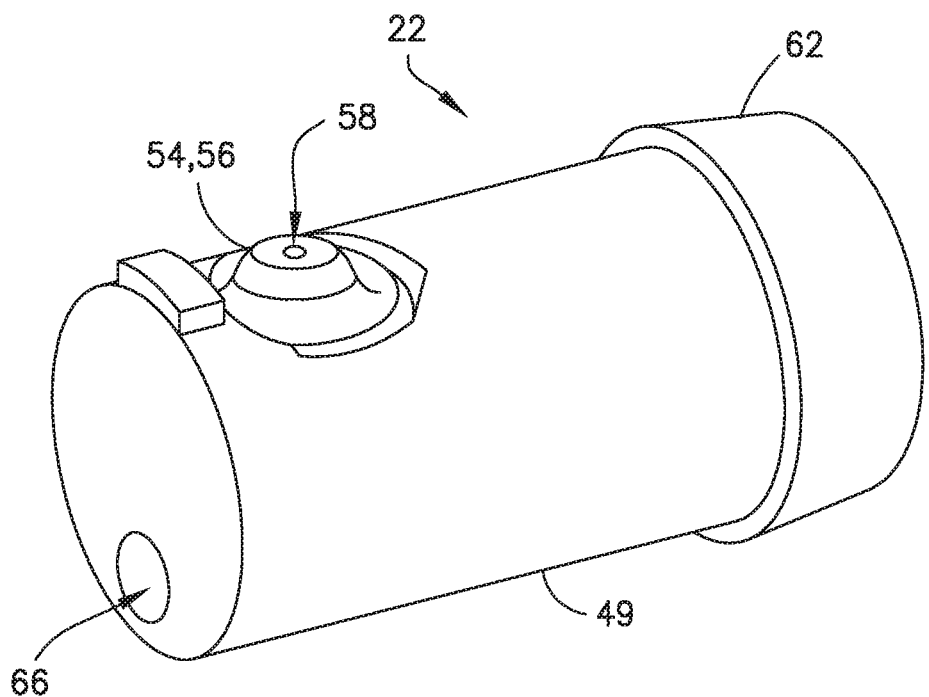
FIG. 7A is a perspective view of an activation module of a blood separation device in a closed position in accordance with an embodiment of the present invention.
Figure 7B:
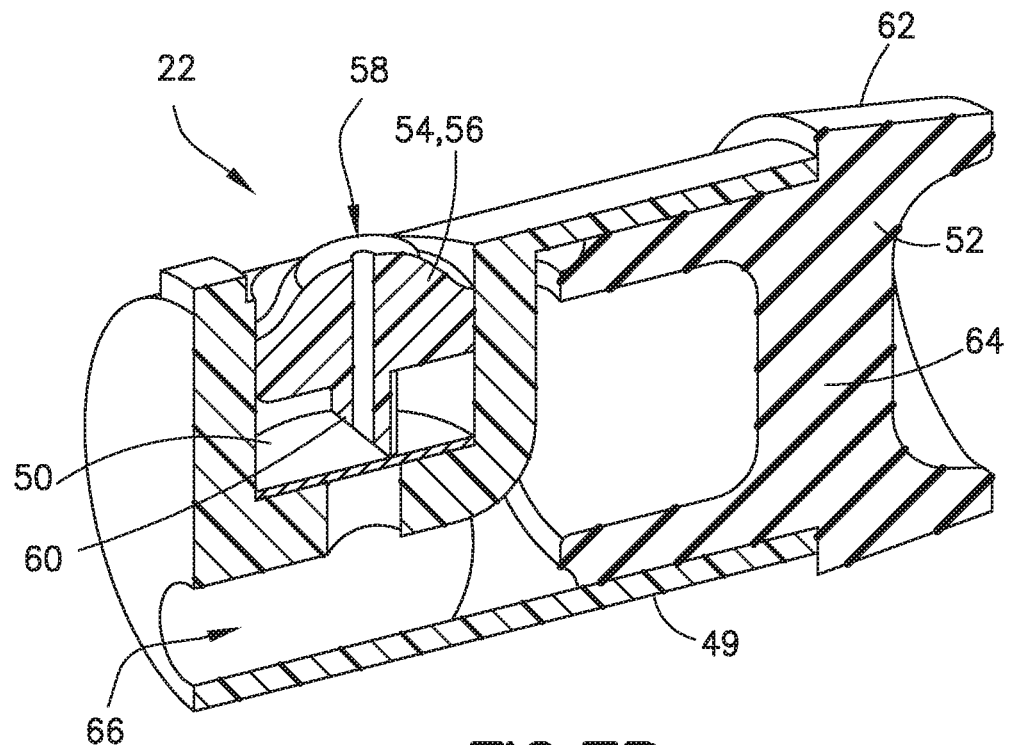
FIG. 7B is a cross-sectional view of the activation module of FIG. 7A in accordance with an embodiment of the present invention.
Figure 8A:
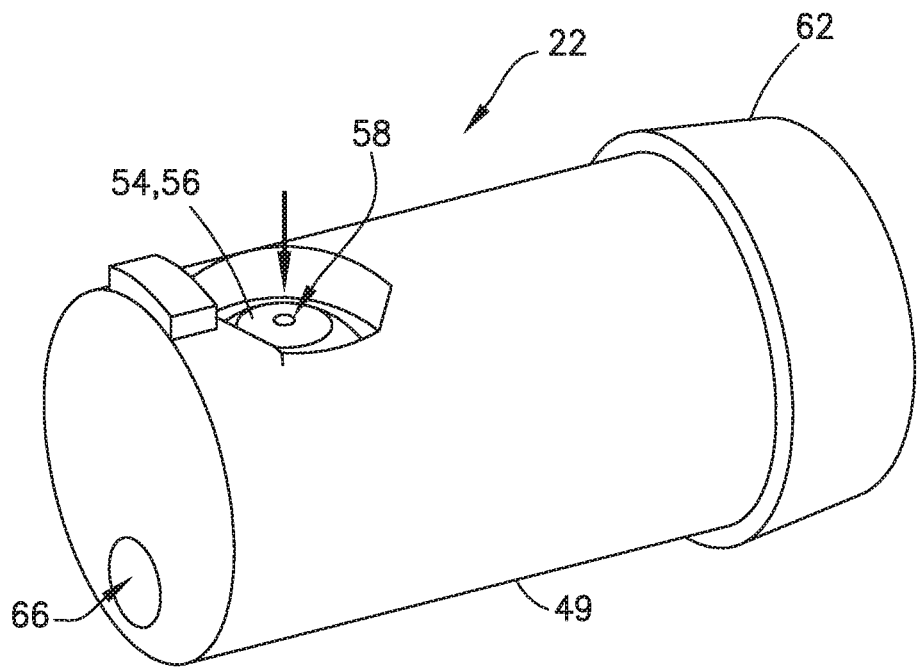
FIG. 8A is a perspective view of an activation module of a blood separation device in an open position in accordance with an embodiment of the present invention.
Figure 8B:
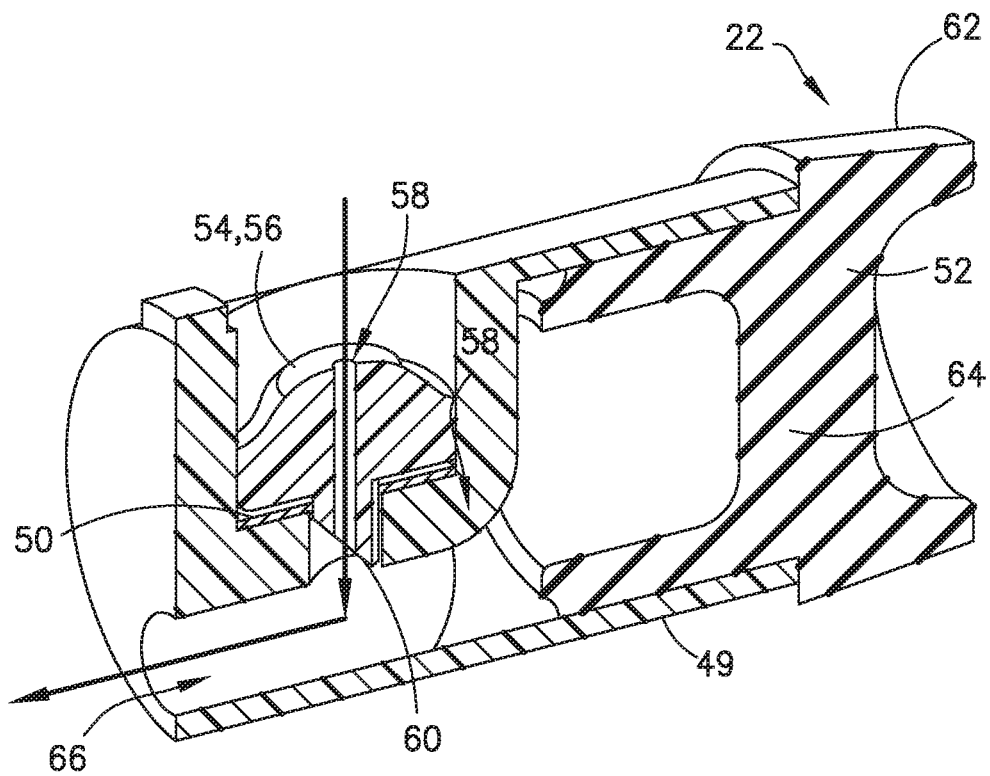
FIG. 8B is a cross-sectional view of the activation module of FIG. 8A in accordance with an embodiment of the present invention.

In an exemplary embodiment, referring to FIGS. 7A-8B, the activation module 22 includes a switch 54. In such an embodiment, actuation of the switch 54 transitions the first seal 50 from the closed position (FIGS. 7A and 7B) to the open position (FIGS. 8A and 8B). Referring to FIGS. 7A-8B, the switch 54 comprises a push button 56 defining a vent hole 58 therethrough and a piercing portion 60. In this manner, actuation of the switch, e.g., depressing or pushing the push button 56 into the position shown in FIGS. 8A and 8B, moves the piercing portion 60 to break the first seal 50 thereby transitioning the first seal 50 to the open position.

With the first seal 50 in the open position, the collection chamber 32 of the sample collection module 20 is in fluid communication with a second pressure P2 via the vent hole 58 of the switch 54. The vent hole 58 provides a venting mechanism for the blood separation device 10. For example, in one embodiment, the piercing portion 60 breaks the first seal 50, e.g., an aluminum foil seal, to create a vent to power the plasma separation process.

The second pressure P2 defined by atmospheric pressure is greater than the first pressure P1 defined within the blood separation device 10, e.g., the collection chamber 32 of the sample collection module 20. In this manner, the pressure difference between the second pressure P2 defined by atmosphere pressure and the residual vacuum in the blood separation device 10, i.e., the first pressure P1 defined within the blood separation device 10, continuously drive the plasma separation process as described in more detail below. Advantageously, using the activation module 22 of the present disclosure, a user can precisely control when the plasma separation process begins.

In an exemplary embodiment, referring to FIGS. 7A-8B, the second seal 52 of the activation module 22 includes a cap 62 having a pierceable self-sealing stopper 64 within a portion of the cap 62. The cap 62 provides a mechanism for allowing the blood separation device 10 to be connectable to a blood collection device 200 (FIG. 3) as described in more detail below.

In one exemplary embodiment, the cap 62 of the present disclosure may be formed substantially similar to a closure described in U.S. Provisional Application 62/666,765, filed May 4, 2018, entitled "Closure for a Biological Fluid Collection Device", the entire disclosure of which is hereby expressly incorporated herein by reference.

Figure 3:
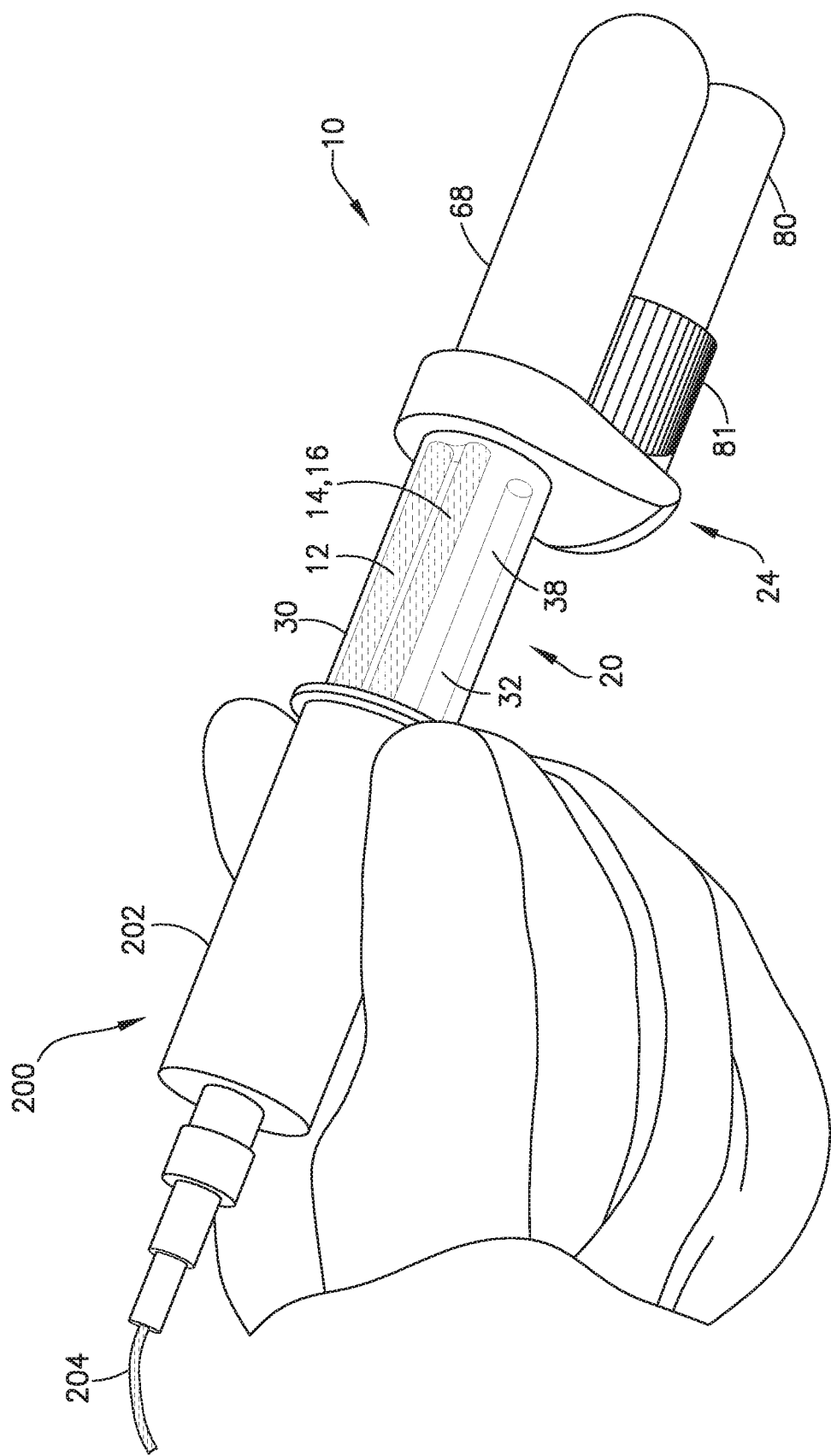
FIG. 3 is a perspective view of a first step of using a system of the present disclosure in accordance with an embodiment of the present invention.

Referring to FIGS. 7A-8B, in one embodiment, the activation module 22 defines an inlet channel 66. Referring to FIG. 3, with a blood collection device 200 connected to the blood separation device 10 via the cap 62, the collection chamber 32 of the sample collection module 20 receives a blood sample 12 via the inlet channel 66. A blood sample 12 flows from the inlet channel 66 of the activation module 22 to the plurality of channels 38 of the collection chamber 32 via the inlet 34.

Referring to FIGS. 1-6 and 11-13, in an exemplary embodiment, the separation module 24 is in fluid communication with the collection chamber 32 of the sample collection module 20 and includes a housing 68 and defines a first chamber 70 having a first volume V1 (FIG. 13) and a second chamber 72 having a second volume V2 (FIG. 13) and including a separation member 74 disposed between the first chamber 70 and the second chamber 72. The first volume V1 of the first chamber 70 and the second volume V2 of the second chamber 72 are different to create a second pressure difference between the first chamber 70 and the second chamber 72 to drive the second phase 16 of a blood sample 12 through the separation member 74 into the second chamber 72 as described in more detail below. In one embodiment, a portion of the separation module 24 forms a microfluidic chip.

Figure 12:
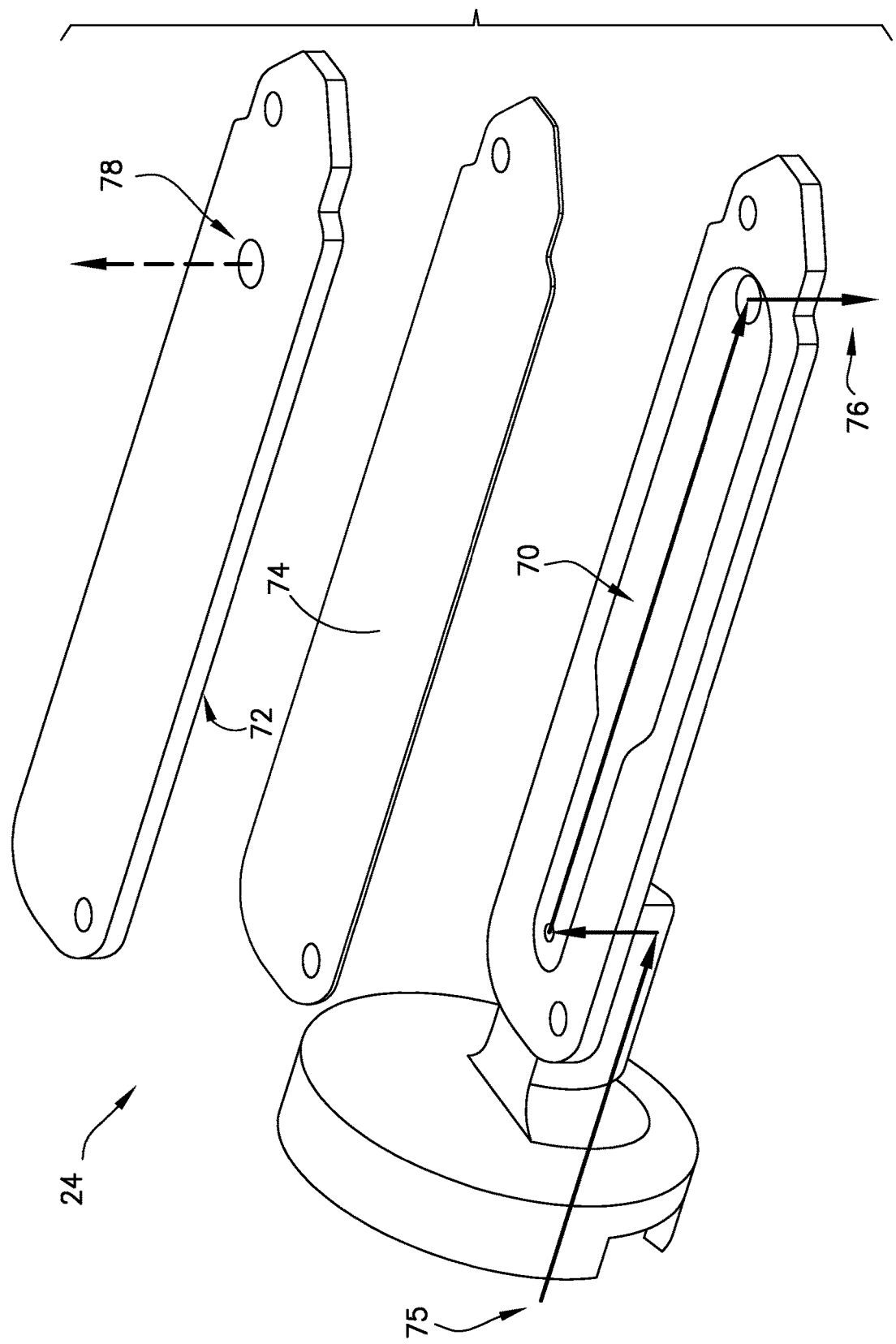
FIG. 12 is a perspective view of a portion of a separation module of a blood separation device in accordance with an embodiment of the present invention.

Referring to FIGS. 11 and 12, in an exemplary embodiment, the separation member 74 traps the first phase 14 in the first chamber 70 and allows the second phase 16 to pass through the separation member 74 into the second chamber 72. In one embodiment, the separation member 74 comprises a track-etched membrane. In certain configurations, the membrane may be less than 100 microns in thickness, such as from 5 to 25 microns in thickness. The membrane may have submicron pores or holes, such as from 0.2 to 0.8 microns in diameter. This dimensionality allows for continuous filtering of a plasma portion of a blood sample flowing parallel to the membrane surface, which prevents clogging of the membrane pores or holes. In other embodiments, the separation member 74 may comprise any filter, and/or any other separation device, that is able to trap the first phase 14 in the first chamber 70 and allow the second phase 16 to pass through the separation member 74 into the second chamber 72.

Referring to FIGS. 11 and 12, the first chamber 70 includes a first chamber inlet 75 and a first chamber outlet 76, and the second chamber 72 includes a second chamber outlet 78. The first chamber inlet 75 is in fluid communication with the exit 36 of the collection channels 38. In this manner, upon actuation of a portion of the activation module 22, a blood sample 12 can flow from the collection chamber 32 of the sample collection module 20 to the first chamber 70 of the separation module 24 for plasma separation.

Referring to FIGS. 1-6, 11, and 13, the separation module 24 of the blood separation device 10 includes a second phase collection container 80 that is in communication with the second chamber outlet 78. The second phase collection container 80 receives the second phase 16 of the blood sample 12. The second phase collection container 80 is able to collect and store the separated second phase 16. Advantageously, referring to FIG. 6, with the second phase 16 contained within the second phase collection container 80, the second phase collection container 80 is removable from the blood separation device 10. In this manner, the second phase 16 of a blood sample 12 can be collected or stored in a secondary second phase container, e.g., a second phase collection container 80, for further diagnostic tests. For example, after separation, with the second phase collection container 80 removed from the blood separation device 10, the second phase collection container 80 is able to transfer the second phase 16 of the blood sample 12 to a point-of-care testing device or other testing device. In an exemplary embodiment, the second phase collection container 80 includes structure allowing the second phase collection container 80 to dispense a portion of the plasma 16, when desired. In one embodiment, the second phase collection container 80 is sealed via a cap or septum 81 to protectively seal the plasma portion 16 within the second phase collection container 80.

Referring to FIG. 11, in an exemplary embodiment, a portion of the second chamber 72 of the separation module 24 is in fluid communication with an interior of the second phase collection container 80 to allow the plasma portion 16 to flow through the separation member 74 and the second chamber 72 into the interior of the second phase collection container 80 for collection.

Figure 13:
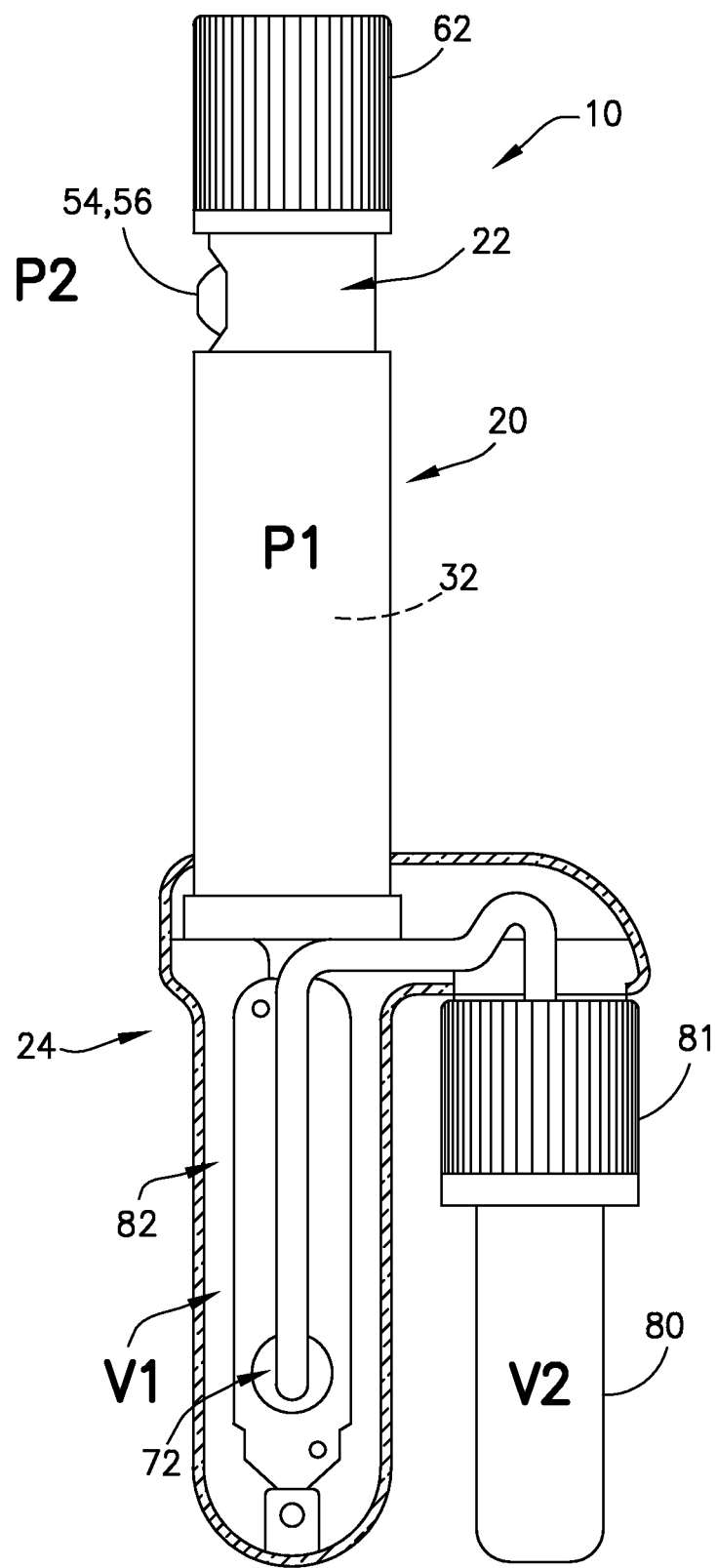
FIG. 13 is a perspective view of a blood separation device in accordance with an embodiment of the present invention.

Referring to FIGS. 11-13, the separation module 24 of the blood separation device 10 also includes a blood sample discard chamber 82 that is in communication with the first chamber outlet 76. The blood sample discard chamber 82 receives the remaining first phase 14 of the blood sample 12 after a blood sample 12 flows over the separation member 74 in the first chamber 70. In this manner, the remaining first phase 14 of the blood sample 12 can be collected and stored in the blood sample discard chamber 82. Also, the blood sample discard chamber 82 ensures that the remaining first phase 14 of the blood sample 12 can be safely stored when the rest of the blood separation device 10 is discarded after use.

Referring to FIGS. 3-6, use of a blood separation device 10 of the present disclosure will now be described.

Referring to FIG. 3, a first step of using a blood separation device 10 of the present disclosure involves collecting a blood sample 12 from a patient, e.g., the blood collection process. For example, first, a given volume of a blood sample 12 from a patient is pulled into the collection chamber 32 of the blood separation device 10 under a vacuum force, immediately following the connection of the blood separation device 10 to a blood collection device 200, such as a tube holder 202. In one embodiment, such a connection consists of a non-patient needle (not shown) of the tube holder 202 piercing the stopper 64 of the cap (FIG. 7B). The opposite end of a line 204 of the tube holder 202 consists of a patient needle of a venous access set in communication with a patient.

Referring to FIG. 3, with the tube holder 202 of the blood collection device 200 connected to the blood separation device 10 via the cap 62 (FIG. 7B), the collection chamber 32 of the sample collection module 20 receives the blood sample 12 via the inlet channel 66 (FIG. 7B) of the activation module 22. The blood separation device 10 of the present disclosure collects and stores a fixed amount of the patient's blood. In one exemplary embodiment, a blood separation device 10 of the present disclosure collects and stores 3 mL of a patient's blood in less than 30 seconds.

The blood sample 12 flows through the inlet channel 66 of the activation module 22 to the collection chamber 32 of the sample collection module 20. Advantageously, during blood collection, the plurality of sequential flow direction alternating collection channels 38 of the collection chamber 32 maximize collection and storage space within the constrained diameter of a blood collection set and also to ensure that the capillary force dominates over gravity during filling.

A user can select one of the ways, sources, or methods that the blood separation device 10 is able to receive a blood sample 12. For example, referring to FIG. 3, the blood separation device 10 of the present disclosure is able to receive a blood sample 12 from a conventional blood collection device 200. For example, the blood collection device 200 may include a tube holder 202 and corresponding venous access set, such as a BD Vacutainer® blood collection tube commercially available from Becton, Dickinson and Company. In other alternative embodiments, blood is collected in a conventional blood collection tube or any other intermediate blood sample container. The blood sample container is then connected to the off-patient separation device to generate plasma.

Once a desired amount of a blood sample 12 is collected into the collection chamber 32 and the blood collection process is complete, the blood separation device 10 is disconnected from the blood collection device 200. In this manner, a blood separation device 10 of the present disclosure decouples and separates the blood collection process from the plasma separation process. Because the plasma separation happens after the blood separation device 10 is disconnected from the patient, the device performance is no longer affected by patient blood pressure and needle gauge, and patient discomfort is greatly reduced.

Upon disconnection of the blood separation device 10 of the present disclosure from the blood collection device 200 and the patient, the collected blood remains stationary in the channels 38 until the plasma separation is activated. The blood separation device 10 accomplishes this by utilizing the second seal 52, e.g., the stopper 64 of the cap 62. The stopper 64 of the cap 62 ensures that the second seal 52 is properly resealed after a needle of the blood collection device 200 is retracted out from the stopper 64 so that there is no pressure difference between the front and back end of the stored blood within the blood separation device 10.

Figure 4:
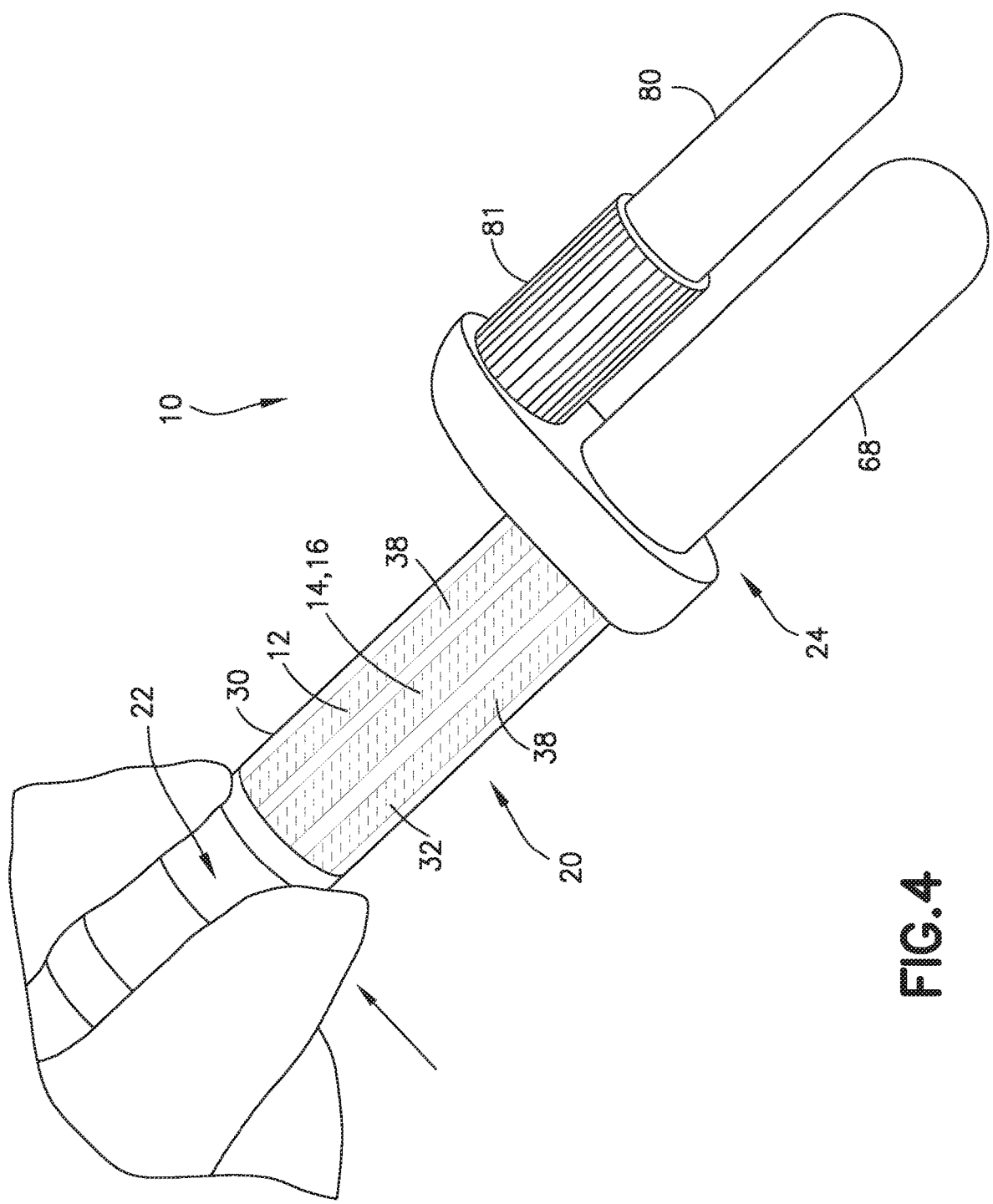
FIG. 4 is a perspective view of a second step of using a system of the present disclosure in accordance with an embodiment of the present invention.

Referring to FIG. 4, after the blood separation device 10 is disconnected from the blood collection device 200, the plasma separation process can be started. Advantageously, the blood separation device 10 of the present disclosure does not require being connected to a patient to perform plasma separation. The plasma separation process is completely controllable and can be started at a convenient and desired time.

Referring to FIG. 4, the plasma separation process is started with the blood separation device 10 off-patient by simply actuating the switch 54 (FIGS. 8A and 8B), e.g., pushing the push button 56, on the blood separation device 10. Actuation of the switch 54 allows the blood separation device 10 to automatically generate plasma 16 from the blood sample 12 stored within the blood separation device 10.

Actuation of the switch 54 transitions the first seal 50 to the open position (FIG. 8B), in which the collection chamber 32 is in fluid communication with a second pressure P2 defined by atmospheric pressure that is greater than the first pressure P1 defined within the collection chamber 32. In this manner, the first pressure difference, e.g., the difference in pressure between the second pressure P2 defined by atmospheric pressure and the first pressure P defined within the collection chamber 32, draws the blood sample 12 into the first chamber 70 of the separation module 24. In other words, the first pressure difference between the atmosphere pressure and the residual vacuum in the blood separation device 10 continuously drives the plasma separation within the blood separation device 10. In an exemplary embodiment, the separation module 24 allows for continuous plasma separation as a blood sample 12 flows through the first chamber 70 and over the separation member 74 by utilizing a cross-flow filtration flow pattern in a microfluidic chip, e.g., the separation module 24 as shown in FIG. 12. In one configuration, the pressure in the collection chamber 32 is limited by the maximum allowable pressure difference across the membrane such that the end point pressure within the collection chamber 32 after blood collection and before filtration should be smaller than 5.5 psi.

Advantageously, the activation module 22 starts the plasma separation process after blood collection and with the blood separation device 10 disconnected from a blood collection device 200 and a patient. To start the plasma separation process after blood collection, it is essential to re-establish a pressure gradient on the stored blood within the collection chamber 32. This is accomplished via the activation module 22 controlling the pressures within the blood separation device 10. Before activation, the first seal 50 and the second seal 52 of the activation module 22 seal the housing 30 of the blood separation device 10 and with the first seal 50 in the closed position (FIG. 7B), the activation module 22 seals the collection chamber 32 at a first pressure P. After activation of the activation module 22, the first seal 50 is transitioned to the open position (FIG. 8B), in which the collection chamber 32 is in fluid communication with a second pressure P2 defined by atmospheric pressure that is greater than the first pressure P1 defined within the collection chamber 32.

Importantly, a second pressure difference is used within the blood separation device 10 to drive the plasma 16 to pass through the separation member 74 into the second chamber 72 and be collected within the second phase collection container 80. With the first seal 50 in the open position (FIG. 8B), the first volume V1 of the first chamber 70 of the separation module 24 and the second volume V2 of the second chamber 72 of the separation module 24 being different provides the second pressure difference between the first chamber 70 and the second chamber 72 to drive the second phase 16 of the blood sample 12 through the separation member 74 into the second chamber 72 and to be collected within the second phase collection container 80. In other words, the second pressure difference across the blood flow in the first chamber 70 and the plasma flow path in the second chamber 72 and their dynamic profiles during the separation provides a power source that further drives the plasma separation process. In an exemplary embodiment, controlling the second pressure difference across the blood flow in the first chamber 70 and the plasma flow path in the second chamber 72 and their dynamic profiles for a given plasma separation chip, e.g., separation module 24, is achieved via setting the appropriate initial vacuum level and balancing the volume ratio of the blood sample discard chamber 82 and the second phase collection container 80. In an exemplary embodiment, a volume of the blood sample discard chamber 82 is designed to ensure that the volume is big enough to have sufficient residual vacuum in the end to drive the blood flow without clogging the separation member 74. In an exemplary embodiment, the volume also needs to be small enough so that at the end of the separation, the pressure in the blood sample discard chamber 82 is higher than a pressure in the second phase collection container 80 to keep the separation member 74 from collapsing. In one configuration, the volume of the blood sample discard chamber 82 is at least twice as large as the volume of the collection chamber 32, and smaller than the volume of the second phase collection container 80 multiplied by the factor (1−yield)/yield. The pressure difference across the membrane may need to be smaller than 5.5 psi at all times during filtration.

Utilizing the first pressure difference and the second pressure difference within the blood separation device 10 forces the blood 12 to flow through the first chamber 70 and over the separation member 74. As the blood 12 flows thru the separation module 24, plasma 16 is continuously separated from the first phase 14 of the blood sample 12.

During plasma separation, the separation member 74 allows the second phase or plasma 16 to pass through the separation member 74 into the second chamber 72 which can be collected or stored in a secondary plasma container, e.g., a second phase collection container 80, for further diagnostic tests. Referring to FIG. 11, the arrow comprising a broken line indicates the second phase flow path 104 that the plasma 16 takes after passing through the separation member 74. In one embodiment, after plasma separation, with the second phase or plasma 16 contained within the second phase collection container 80, the second phase collection container 80 is removable from the blood separation device 10. The second phase collection container 80 can then be used to transfer the plasma portion 16 to a point-of-care testing device or other diagnostic testing system.

During plasma separation, the separation member 74 traps the first phase 14 of the blood sample 12 within the first chamber 70, e.g., the first phase 14 of the blood sample 12 is not allowed to pass through the separation member 74 into the second chamber 72. Referring to FIG. 11, the arrow comprising a straight line indicates the flow path 102 that the blood sample 12 takes through the collection chamber 32 and the flow path 102 that the first phase 14 of the blood sample 12 takes after passing over the separation member 74 and to the blood sample discard chamber 82. Referring to FIGS. 11 and 12, the first phase 14 of the blood sample 12 flows into the first chamber 70 through the first chamber inlet 75 and over the separation member 74 surface, and then exits the first chamber 70 via the first chamber outlet 76 into the blood sample discard chamber 82.

In one exemplary embodiment, a blood separation device 10 of the present disclosure is able to generate 350 to 600 uL of plasma 16 from the stored 3 mL of blood in less than 7 minutes.

Referring to FIG. 5, the blood separation device 10 of the present disclosure allows for plasma separation to occur independent of an orientation of the blood separation device 10. In other words, the blood separation device 10 separates plasma regardless of whether the blood separation device 10 is in an upright orientation, e.g., the blood separation device 10 is contained in a tube rack, or if the blood separation device 10 is lying in a flat orientation on a table or tray.

Referring to FIG. 6, with the second phase or plasma 16 contained within the second phase collection container 80, the second phase collection container 80 is removable from the blood separation device 10. The second phase collection container 80 can then be used to transfer the plasma portion 16 to a point-of-care testing device or other diagnostic testing system. In one embodiment, the second phase collection container 80 is removably connectable to the blood separation device 10 via a luer lock septum seal.

In other words, after plasma separation is completed, the plasma 16 within the second phase collection container 80 is removed from the blood separation device 10 for use in clinical tests. The rest of the blood separation device 10 can then be discarded.

As described herein, the present disclosure provides a blood separation device that decouples and separates the blood collection process from the plasma separation process. The blood separation device includes a sample collection module, an activation module, and a separation module. Because the plasma separation happens after the blood separation device is disconnected from the patient, the device performance is no longer affected by patient blood pressure and needle gauge, and patient discomfort is greatly reduced.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A blood separation device adapted to receive a blood sample having a first phase and a second phase, the blood separation device comprising:
   a sample collection module having a housing defining a collection chamber;
   an activation module connected to the sample collection module, the activation module having a first seal, the first seal transitionable from a closed position in which the collection chamber has a first pressure to an open position, by actuation of a portion of the activation module, in which the collection chamber is in fluid communication with a second pressure greater than the first pressure;
   a second seal for sealing the housing; and
   a separation module in fluid communication with the collection chamber of the sample collection module, the separation module comprising a blood sample discharge chamber having a first volume, a second phase collection container having a second volume, and a separation member disposed between the blood sample discharge chamber and the second phase collection container, wherein the first volume and the second volume are different, wherein the blood sample flows from the collection chamber into the separation member, the blood sample discharge chamber receives the first phase from the separation member, and the second phase collection container receives the second phase from the separation member.

2. The blood separation device of claim 1, wherein the activation module includes a switch, wherein actuation of the switch transitions the first seal to the open position.

3. The blood separation device of claim 2, wherein the switch comprises a push button defining a vent hole therethrough and a piercing portion, wherein actuation of the switch moves the piercing portion to break the first seal thereby transitioning the first seal to the open position.

4. The blood separation device of claim 3, wherein with the first seal in the open position, the collection chamber of the sample collection module is in fluid communication with atmospheric pressure via the vent hole of the switch.

5. The blood separation device of claim 1, wherein the second seal comprises a cap having a pierceable self-sealing stopper within a portion of the cap.

6. The blood separation device of claim 5, wherein the blood separation device is connectable to a blood collection device via the cap.

7. The blood separation device of claim 6, wherein the activation module defines an inlet channel, and wherein with the blood collection device connected to the blood separation device via the cap, the collection chamber receives the blood sample via the inlet channel.

8. The blood separation device of claim 7, wherein the collection chamber includes an inlet end and an exit end and defines a plurality of sequential flow direction alternating collection channels.

9. The blood separation device of claim 8, wherein the inlet end of the collection chamber is in fluid communication with the inlet channel of the activation module.

10. The blood separation device of claim 7, wherein the collection chamber includes an inlet end and an exit end and defines a first collection channel extending from the inlet end to the exit end, a second collection channel in communication with a portion of the first collection channel and extending from the exit end to the inlet end, and a third collection channel in communication with a portion of the second collection channel and extending from the inlet end to the exit end.

11. The blood separation device of claim 10, wherein the blood sample travels through the first collection channel in a first direction, the blood sample travels through the second collection channel in a second direction opposite the first direction, and the blood sample travels through the third collection channel in a third direction opposite the second direction.

12. The blood separation device of claim 10, wherein the first collection channel is spaced from the second collection channel which is spaced from the third collection channel.

13. The blood separation device of claim 7, wherein, with the blood collection device disconnected from the blood separation device, and wherein upon actuation of the switch to transition the first seal to the open position, a pressure difference between the second pressure defined by atmospheric pressure and the first pressure defined within the collection chamber forces the blood sample through the separation device.

14. The blood separation device of claim 1, wherein the separation member comprises a first chamber having a first chamber inlet and a first chamber outlet, a second chamber having a second chamber outlet, and a separation member disposed between the first chamber and the second chamber.

15. The blood separation device of claim 14, wherein with the first seal in the open position, the first volume and the second volume being different provides a pressure difference between the first chamber and the second chamber to drive the phase of the blood sample through the separation member into the second chamber.

16. The blood separation device of claim 15, wherein the separation member traps the first phase in the first chamber and allows the second phase to pass through the separation member into the second chamber.

17. The blood separation device of claim 14, wherein the second phase collection container is in communication with the second chamber outlet.

18. The blood separation device of claim 14, wherein the blood sample discard chamber is in communication with the first chamber outlet.

19. The blood separation device of claim 14, wherein the separation member comprises a track-etched membrane.

20. The blood separation device of claim 14, wherein with the first seal in the open position, the first volume and the second volume being different provides a pressure difference between the first chamber and the second chamber that drives the second phase of the blood sample through the separation member into the second chamber.

21. The blood separation device of claim 20, wherein, with the second phase contained within the second phase collection container, the second phase collection container is removable from the blood separation device.

22. The blood separation device of claim 1, wherein with the second seal in the open position, a negative pressure defined within the collection chamber draws the blood sample into the collection chamber.

23. The blood separation device of claim 1, wherein the first phase is a cellular portion and the second phase is a plasma portion.

* * * * *

UNITED STATES PATENT AND TRADEMARK OFFICE
CERTIFICATE OF CORRECTION

PATENT NO. : 12,076,146 B2
APPLICATION NO. : 17/059598
DATED : September 3, 2024
INVENTOR(S) : Peng Li et al.

It is certified that error appears in the above-identified patent and that said Letters Patent is hereby corrected as shown below:

In the Claims

Column 16, Line 23, Claim 15, delete "phase" and insert -- second phase --

Signed and Sealed this
Twenty-second Day of October, 2024

Katherine Kelly Vidal
*Director of the United States Patent and Trademark Office*